United States Patent [19]

Hitzel et al.

[11] Patent Number: 4,542,139
[45] Date of Patent: Sep. 17, 1985

[54] SULFONYLUREAS PHARMACEUTICAL FORMULATIONS BASED ON THESE COMPOUNDS AND THEIR USE FOR TREATMENT OF DIABETES

[75] Inventors: Volker Hitzel, Hofheim am Taunus; Rudi Weyer, Kelkheim (Taunus); Karl Giesen, Frankfurt am Main; Harald Ritzel, Mainz, all of Fed. Rep. of Germany

[73] Assignee: Hoechst Aktiengesellschaft, Frankfurt am Main, Fed. Rep. of Germany

[21] Appl. No.: 603,987

[22] Filed: Apr. 26, 1984

Related U.S. Application Data

[63] Continuation of Ser. No. 413,561, Aug. 31, 1982, abandoned.

[30] Foreign Application Priority Data

Sep. 2, 1981 [DE] Fed. Rep. of Germany ....... 3134780

[51] Int. Cl.$^4$ ..................... A61K 31/47; C07D 215/54
[52] U.S. Cl. .................................... 514/312; 546/156
[58] Field of Search ......................... 546/156; 424/258

[56] References Cited

U.S. PATENT DOCUMENTS

| | | | |
|---|---|---|---|
| 4,132,795 | 1/1979 | Hitzel et al. | 546/156 |
| 4,282,239 | 8/1981 | Weyer et al. | 424/274 |
| 4,315,940 | 2/1982 | Hitzel et al. | 424/258 |
| 4,379,785 | 4/1983 | Weyer et al. | 424/258 |

FOREIGN PATENT DOCUMENTS 357560 7/1980 Austria .
2114629 10/1971 Fed. Rep. of Germany .

*Primary Examiner*—Donald G. Daus
*Assistant Examiner*—Diana G. Rivers
*Attorney, Agent, or Firm*—Curtis, Morris & Safford

[57] ABSTRACT

Sulfonylureas of the formula

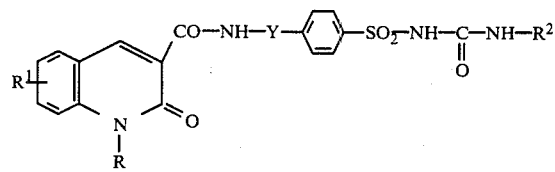

in which Y denotes alkylene having 2–3 C atoms, R denotes alkyl having 1–4 C atoms, $R^1$ denotes hydrogen, chlorine or methyl, and $R^2$ denotes alkyl having 3–6 C atoms, cycloalkyl, alkylcycloalkyl, cycloalkylalkyl, cycloalkenyl, alkylcycloalkenyl or cycloalkenylalkyl, each having 5–8 C atoms, and their physiologically tolerated salts, and processes for their preparation and medicaments prepared therefrom.

4 Claims, No Drawings

SULFONYLUREAS PHARMACEUTICAL FORMULATIONS BASED ON THESE COMPOUNDS AND THEIR USE FOR TREATMENT OF DIABETES

This application is a continuation of application Ser. No. 413,561, filed Aug. 31, 1982.

The invention relates to sulfonylureas of the formula

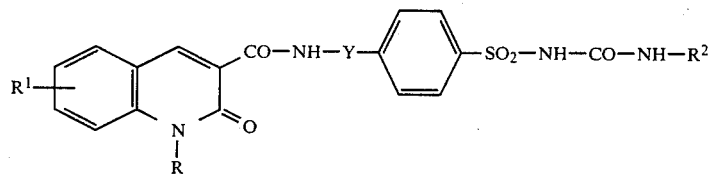

which as the substance or in the form of their physiologically tolerated salts have hypoglycemic properties and which are distinguished by a powerful lowering of the level of sugar in the blood and thus can be used as medicaments.

In the formula: Y denotes alkylene having 2-3 C atoms, R denotes alkyl having 1-4 C atoms, $R^1$ denotes hydrogen, chlorine or methyl, and $R^2$ denotes alkyl having 3-6 C atoms, cycloalkyl, alkylcycloalkyl, cycloalkylalkyl, cycloalkenyl, alkylcycloalkenyl or cycloalkenylalkyl, each having 5-8 C atoms.

In the general formula: Y preferably denotes —CH$_2$—CH$_2$—, R preferably denotes methyl, $R^1$ preferably denotes hydrogen and $R^2$ preferably denotes cyclohexyl.

In addition, the invention relates to processes for the preparation of these sulfonylureas, pharmaceutical formulations containing these compounds or which are composed of them and their use for the treatment of diabetes.

The processes for the preparation of the sulfonylureas and their salts comprise (a) reacting benzenesulfonylcarbamic acid derivatives substituted in the 4-position with the group

with an amine $R^2$—NH$_2$ or its salts or reacting sulfonamides of the formula

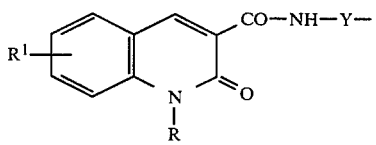

or their salts with a carbamic acid derivative substituted by $R^2$, (b) cleaving benzenesulfonyl-isourea ethers, -isothiourea ethers, -parabanic acids or -halogenoformamidines substituted with the group

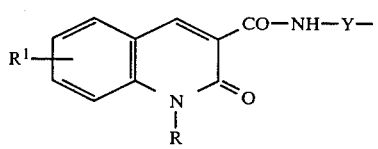

(c) replacing the sulfur atom by oxygen in benzenesulfonylthioureas substituted by

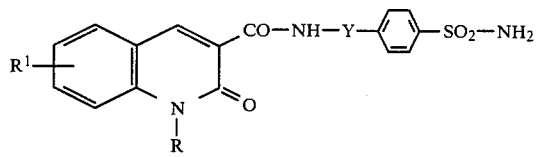

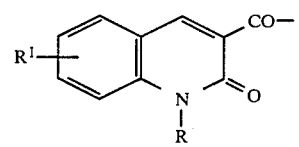

(d) oxidizing correspondingly substituted benzenesulfinyl- or -sulfenyl-ureas (e) introducing the radical

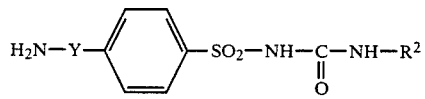

into benzenesulfonylureas of the formula $$H_2N-Y-\text{[phenyl]}-SO_2-NH-\underset{\underset{O}{\|}}{C}-NH-R^2$$

optionally in steps, (f) reacting correspondingly substituted benzenesulfonyl halides with $R^2$-substituted ureas or their alkali metal salts or reacting correspondingly substituted benzenesulfinyl halides or, in the presence of acid condensing agents, correspondingly substituted sulfinic acids or their alkali metal salts, with N-$R^2$-N'-hydroxyurea, optionally converting the salts obtained into the free compounds or optionally treating the reaction products with alkaline agents to form salts.

The benzenesulfonylcarbamic acid derivatives mentioned in process (a) are, for example, benzenesulfonylcarbamic acid esters, -thiolcarbamic acid esters, -ureas, -semicarbazides or -semicarbazones. The reaction of benzenesulfonylcarbamic acid esters with amines is preferably used.

The $R^2$-substituted carbamic acid derivatives used for the reaction of the benzenesulfonamides substituted in the 4-position are, for example, the corresponding isocyanates, carbamic acid esters, thiolcarbamic acid esters, carbamic acid halides or ureas. Of these, the reaction of the sulfonamides with isocyanates or carbamic acid chlorides is preferably used.

The benzenesulfonyl-carbamic acid esters or -thiolcarbamic acid esters mentioned have, in the alcohol component, an alkyl radical or an aryl radical or a heterocyclic radical. Since this radical is split off during the reaction, its chemical constitution has no effect on the character of the final product and can thus be varied within wide limits. The same applies to the N-R$^2$-substituted carbamic acid esters or the corresponding thiolcarbamic acid esters.

On the part of the urea molecule distant from the sulfonyl group, the benzenesulfonylureas suitable as starting materials in the process are unsubstituted or are substituted once or, in particular, twice. Since these substituents are split off during the reaction with amines, their character can be varied within wide limits. Apart from benzenesulfonylureas with alkyl, aryl, acyl or heterocyclic substituents, benzenesulfonylcarbamoylimidazoles and similar compounds or bisbenzenesulfonylureas, which can have another substituent, for example methyl, on one of the nitrogen atoms, are also suitable. For example, bisbenzenesulfonylureas or N-benzenesulfonyl-N'-acylureas of these types are treated with R$^2$-substituted amines and the salts obtained are heated at elevated temperatures, in particular those above 100° C.

In addition, R$^2$-substituted ureas or those R$^2$-substituted ureas which are substituted once or, in particular, twice on the free nitrogen atom are suitable as starting compounds for the reaction with benzenesulfonamides substituted in the 4-position by

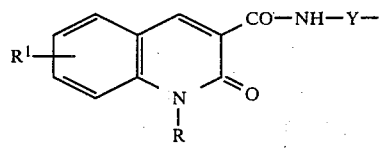

Examples of suitable starting materials of this type are N-cyclohexylurea, the corresponding N'-acetyl-, N'-nitro-, N'-cyclohexyl-, N',N'-diphenyl- (it also being possible for the two phenyl radicals to be substituted, or to be bonded to one another directly or via a bridging member, such as —CH$_2$—, —NH—, —O— or —S—), N'-methyl-N'-phenyl-, N',N'-dicyclohexylureas and also cyclohexyl-carbamoylimidazoles, -pyrazoles or -triazoles and also those of the compounds mentioned which have another substituent, which is within the range of the definition of R$^2$, instead of cyclohexyl.

The cleavage of the benzenesulfonylparabanic acids, -isourea ethers, -isothiourea ethers or -halogenoformamidines mentioned as starting materials in process (b) is advantageously carried out in the presence of bases. Isourea ethers can also be cleaved with good results in an acid medium.

The replacement of the sulfur atom in the thiourea grouping of correspondingly substituted benzenesulfonylthioureas by an oxygen atom is carried out in a known manner, for example with the aid of oxides or salts of heavy metals or by using oxidizing agents, such as hydrogen peroxide, sodium peroxide, nitrous acid or permanganates. Thioureas are also desulfurized by treatment with phosgene or phosphorus pentachloride. Chloroformamidines or carbodiimides obtained as intermediates are converted by suitable measures, such as saponification or addition of the elements of water, into the benzenesulfonylureas.

The oxidation of benzenesulfinyl- or benzenesulfenylureas is carried out by a known method, preferably with oxidizing agents, such as permanganate or hydrogen peroxide.

The acylation of the sulfonylureas according to process (e) is carried out with reactive derivatives of the acid

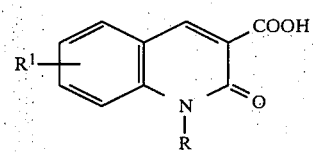

such as, for example, halides, mixed anhydrides or active esters.

Particularly suitable sulfonyl or sulfinyl halides according to process (f) are the chlorides. Examples of acid condensing agents used are thionyl chloride and polyphosphoric acid.

The preparation of the physiologically tolerated salts is carried out by known method. Alkali metal hydroxides, carbonates or bicarbonates and alkaline earth metal hydroxides, carbonates or bicarbonates and physiologically tolerated organic bases are particularly suitable for salt formation.

In general, the embodiments of the process according to the invention can be widely varied in respect of the reaction conditions and can be adjusted to the particular situation. For example, the reactions are carried out in the absence or presence of solvents, and at room temperature or at elevated temperature.

Depending on the characteristics of the starting materials, one or other of the processes described may, in particular cases, provide a desired individual benzenesulfonylurea only in small yields or it may be little suited for its synthesis. In such cases, which occur relatively seldom, it is no problem for the specialist to synthesize the desired product by another of the procedures described.

The 1-substituted 1,2-dihydro-2-oxoquinoline-3-carboxylic acids serving as starting materials are known from the literature. The corresponding 1,6-disubstituted 1,2-dihydro-2-oxoquinoline-3-carboxylic acids can be prepared in an analogous manner.

The compounds obtained are preferably purified by reprecipitation and/or recrystallization. Another method of purification comprises liberating the substance from a crystalline (alkali metal) salt in a suitable solvent.

The compounds according to the invention are distinguished by valuable pharmacological properties, in particular hypoglycemic properties. Thus they are suitable as medicaments, in particular as antidiabetics.

The hypoglycemic activity of these benzenesulfonylureas according to the invention is demonstrated, for example, by feeding them as free compounds or in the form of the sodium salts to rabbits which are fed normally and finding the blood sugar value by the known method of Hagedorn-Jensen or with an autoanalyzer over a relatively long period of time.

Routine determination of the hypoglycemic activity is carried out, for example, with dosages of, for example, 10 mg or 2 mg or 0.4 mg of active substance per kg of experimental animal by known methods. The following compounds I to IV were administered orally in doses of 2 mg/kg to rabbits and the blood sugar values were determined over a prolonged period of time using an autoanalyzer. The lowering in the blood sugar level measured here is given in % after ... hours in the following table:

I. N-(4-<2-(1-methyl-1,2-dihydro-2-oxo-quinoline-3-carboxamido)-ethyl>-benzenesulfonyl)-N'-cyclohexylurea sodium salt II. N-(4-<2-(1-methyl-1,2-dihydro-2-oxo-6-chloro-quinoline-3-carboxamido)-ethyl>-benzenesulfonyl)-N'-butylurea III. N-(4-<2-(1-methyl-1,2-dihydro-2-oxo-quinoline-3-carboxamido)-ethyl>-benzenesulfonyl)-N'-cyclopentyl-urea IV. N-(4-<2-(1-methyl-1,2-dihydro-2-oxo-quinoline-3-carboxamido)-ethyl>-benzenesulfonyl)-N'-(3-methylcyclopentyl)-urea

TABLE

| Compound | Lowering in the blood sugar level in rabbits after oral administration of 2 mg/kg in % after | | | | |
|---|---|---|---|---|---|
| | 1 | 3 | 5 | 24 | 48 hours |
| I | 32 | 35 | 34 | 28 | 28 |
| II | 34 | 38 | 39 | 35 | 0 |
| III | 34 | 43 | 44 | 42 | 26 |
| VI | 26 | 31 | 34 | 37 | 5 |

The benzenesulfonylureas according to the invention are distinguished by a strong hypoglycemic activity. In addition, the compounds are well tolerated.

The properties of the compounds permit the use, in the therapy of diabetes mellitus, of doses which are so small that the formulation only normalizes the previously lowered response of the pancreas to an increased level of sugar in the blood.

The sulfonylureas described preferably serve for the preparation of formulations for the treatment of diabetes mellitus by oral administration. They are administered as such or in the form of their salts, or in the presence of substances which lead to salt formation. Alkaline agents, such as alkali metal hydroxides, carbonates or bicarbonates or alkaline earth metal hydroxides, carbonates or bicarbonates, for example, are used for salt formation. The formulations can also contain other active compounds in addition to the sulfonylurea or its salt. Suitable medical formulations are preferably tablets which, in addition to the sulfonylureas or their salts, contain the customary excipients and auxiliaries, such as talc, starch, lactose or magnesium stearate. In this context, it can be advantageous to employ the active compound or compounds in a ground or finely precipitated form or as a mixture of these forms. A formulation which contains the benzenesulfonylureas according to the invention as the active compound, for example a tablet or a powder, with or without additives, is preferably converted into a suitably dosed form. For this purpose, the dose selected is that adjusted to the effectiveness of the benzenesulfonylurea used and the desired effect. Advantageously, the dosage per unit is about 0.5 to 50 mg, preferably 1 to 20 mg, but dosage units can also be used which are larger or smaller than this and these should be divided or multiplied as required before administration.

The following examples show some of the numerous variants of the process which are suitable for the synthesis of the sulfonylureas according to the invention. However, they are not intended to represent a restriction of the subject of the invention.

EXAMPLE 1

Potassium salt of N-(4-<2-(1-methyl-1,2-dihydro-2-oxoquinoline-3-carboxamido)ethyl>benzenesulfonyl)-N'-cyclohexylurea 38.54 g of 4-(2-<1-methyl-1,2-dihydro-2-oxoquinoline-3-carboxamido>ethyl)benzenesulfonamide (melting point 235°–237° C., prepared by the reaction of 1-methyl-1,2-dihydro-2-oxoquinolinecarboxylic acid with methyl chloroformate and triethylamine and subsequent reaction with 4-(2-aminoethyl)benzenesulfonamide) were suspended in 2 l of butan-2-one. After the addition of 27.6 g of ground anhydrous potassium hydroxide and 14.0 ml of cyclohexyl isocyanate, the mixture was stirred under reflux for 5 hours. After cooling down, the potassium salts were filtered off with suction and dried. They were then suspended in 50 ml of water and the mixture was adjusted to pH 7.5 with 2N hydrochloric acid, with stirring. The solid was again filtered off with suction and extracted by boiling with 500 ml of ethanol. The potassium salt of N-(4-<2-(1-methyl-1,2-dihydro-2-oxoquinoline-3-carboxamido)-ethyl>benzenesulfonyl)-N'-cyclohexylurea thus obtained, after drying, melted at 281°–283° C.

The following compounds were obtained in an analogous manner:

Potassium salt of N-(4-<2-(1-methyl-1,2-dihydro-2-oxoquinoline-3-carboxamido)ethyl>benzenesulfonyl)-N'-$\Delta^3$-cyclohexylurea, of melting point 259°–261° C. (from ethanoldimethylformamide);

Potassium salt of N-(4-<2-(1-methyl-1,2-dihydro-2-oxoquinoline-3-carboxamido)ethyl>benzenesulfonyl)-N'-cyclooctylurea, of melting point 262°–264° C. (from ethanol).

EXAMPLE 2

N-(4-<2-(1-Methyl-1,2-dihydro-2-oxoquinoline-3-carboxamido)-ethyl>benzenesulfonyl)-N'-cyclohexylurea 8.7 g of 4-(2-<1-methyl-1,2-dihydro-2-oxoquinoline-3-carboxamido>ethyl)benzenesulfonamide (prepared as indicated in Example 1) were suspended in 100 ml of acetone and 11.25 ml of 2N sodium hydroxide solution. After cooling down to 0°–5° C., a solution of 3.1 g of cyclohexyl isocyanate in 10 ml of acetone was added dropwise. The mixture was stirred at 0°–5° C. for 1 hour and at room temperature for 4 hours and the precipitate was brought to solution by dilution with water. After filtration, the filtrate was acidified with 2N hydrochloric acid, the precipitate was filtered off with suction and recrystallized from ethanol/dimethylformamide. The melting point of the N-(4-<2-(1-methyl-1,2-dihydro-2-oxoquinoline-3-carboxamido)-ethyl>benzenesulfonyl)-N'-cyclohexylurea was 213°–215° C.

EXAMPLE 3

Sodium salt of N-(4-<2-(1-methyl-1,2-dihydro-2-oxoquinoline-3-carboxamido)ethyl>benzenesulfonyl)-N'-cyclohexylurea 4.0 g of the N-(4-<2-(1-methyl-1,2-dihydro-2-oxoquinoline-3-carboxamido)ethyl>benzenesulfonyl)-N'-cyclohexylurea obtained in Example 2 were introduced in portions into a mixture of 100 ml of methanol and 3.91 ml of 2N sodium hydroxide solution. After a short subsequent period of stirring, the crystalline sodium salt precipitated. This was filtered off with suction, treated with hot ethanol and dried. The melting point was 291°–293° C.

EXAMPLE 4

N-(4-<2-(1-Methyl-1,2-dihydro-2-oxoquinoline-3-carboxamido)ethyl>benzenesulfonyl)-N'-(4-methylcyclohexyl)urea 2.9 g of 4-(2-<1-methyl-1,2-dihydro-2-oxoquinoline-3-carboxamido>ethyl)benzenesulfonamide (prepared as indicated in Example 1) were suspended in 150 ml of butan-2-one together with 2.07 g of ground anhydrous potassium hydroxide. After adding 1.25 g of 4-methylcyclohexyl isocyanate, the mixture was stirred under reflux for 4 hours. The mixture was cooled down and filtered off with suction, and the precipitate was suspended in 150 ml of water and acidified with dilute hydrochloric acid. The precipitated N-(4-<2-(1-methyl-1,2-dihydro-2-oxoquinoline-3-carboxamido)-ethyl>-benzenesulfonyl)-N'-(4-methylcyclohexyl)urea was filtered off with suction, extracted by boiling with ethanol and dried. It melted at 221°–223° C.

The following compounds were obtained in an analogous manner:

N-(4-<2-(1-Methyl-1,2-dihydro-2-oxoquinoline-3-carboxamido)ethyl>benzenesulfonyl)-N'-cyclopentylurea, of melting point 197°–199° C. (from ethanol-dimethylformamide);

N-(4-<2-(1-Methyl-1,2-dihydro-2-oxoquinoline-3-carboxamido)ethyl>benzenesulfonyl)-N'-cyclopentylmethylurea, of melting point 218°–220° C. (from ethanol-dimethylformamide);

N-(4-<2-(1-Methyl-1,2-dihydro-2-oxoquinoline-3-carboxamido)ethyl>benzenesulfonyl)-N'-cycloheptylurea, of melting point 209°–211° C. (from ethanol-dimethylformamide);

N-(4-<2-(1-Methyl-1,2-dihydro-2-oxoquinoline-3-carboxamido)ethyl>benzenesulfonyl)-N'-(3-methylcyclopentyl)urea, of melting point 204°–206° C. (from ethanol-dimethylformamide);

N-(4-<2-(1-Methyl-1,2-dihydro-2-oxoquinoline-3-carboxamido)ethyl>benzenesulfonyl)-N'-hexylurea, of melting point 202°–204° C. (from ethanol-dimethylformamide);

N-(4-<2-(1-Methyl-1,2-dihydro-2-oxoquinoline-3-carboxamido)ethyl>benzenesulfonyl)-N'-propylurea, of melting point 203°–205° C. (from ethanol-dimethylformamide).

The following compound is obtained in an analogous manner from 4-(2-<1-ethyl-1,2-dihydro-2-oxoquinoline-3-carboxamido>ethyl)benzenesulfonamide (melting point 199°–200° C., prepared in analogy to Example 1):

N-(4-<2-(1-Ethyl-1,2-dihydro-2-oxoquinoline-3-carboxamido)-ethyl>benzenesulfonyl)-N'-cyclohexylurea, of melting point 157°–158° C. (from ethanol-dimethylformamide).

The following compound is obtained in an analogous manner from 4-(2-<1-butyl-1,2-dihydro-2-oxoquinoline-3-carboxamido>ethyl)benzenesulfonamide (melting point 290°–294° C., prepared in analogy to Example 1):

N-(4-<2-(1-Butyl-1,2-dihydro-2-oxoquinoline-3-carboxamido)-ethyl>benzenesulfonyl)-N'-cyclohexylurea, of melting point 179°–181° C. (from ethanol).

EXAMPLE 5

N-(4-<2-(1-Methyl-1,2-dihydro-2-oxo-6-chloroquinoline-3-carboxamido)ethyl>benzenesulfonyl)-N'-cyclohexylurea 2.5 g of 4-(2-<1-methyl-1,2-dihydro-2-oxo-6-chloroquinoline-3-carboxamido>ethyl)benzenesulfonamide (melting point 237°–239° C., prepared in an analogous manner to that indicated in Example 1 from 1-methyl-1,2-dihydro-2-oxo-6-chloroquinoline-3-carboxylic acid and 4-(2-aminoethyl)-benzenesulfonamide) were suspended in 150 ml of butan-2-one. After adding 1.66 g of anhydrous ground potassium hydroxide and 0.82 g of cyclohexyl isocyanate, the mixture was stirred under reflux for 4 hours. After cooling down, the residue was filtered off then suspended in water and the mixture was acidified with dilute hydrochloric acid. The N-(4-<2-(1-methyl-1,2-dihydro-2-oxo-6-chloroquinoline-3-carboxamido)ethyl>benzenesulfonyl)-N'-cyclohexylurea thus precipitated was recrystallized from ethanol-dimethylformamide and melted at 209°–210° C.

The following compound is obtained in an analogous manner:

N-(4-<2-(1-Methyl-1,2-dihydro-2-oxo-6-chloroquinoline-3-carboxamido)ethyl>benzenesulfonyl)-N'-butylurea, of melting point 157°–158° C. (from methanol-dimethylformamide).

EXAMPLE 6

N-(4-<2-(1,6-Dimethyl-1,2-dihydro-2-oxoquinoline-3-carboxamido)ethyl>benzensulfonyl)-N'-cyclohexylurea 3.0 g of 4-(2->1,6-dimethyl-1,2-dihydro-2-oxoquinoline-3-carboxamido>ethyl)benzenesulfonamide (melting point 234°–236° C., prepared in an analogous manner to that indicated in Example 1 from 1,6-dimethyl-1,2-dihydro-2-oxoquinoline-3-carboxylic acid and 4-(2-aminoethyl)-benzenesulfonamide) together with 2.07 g of anhydrous ground potassium hydroxide were stirred under reflux in 150 ml of butan-2-one and 1.03 g of cyclohexyl isocyanate for 4 hours. After cooling down, the mixture was filtered, the salts were dissolved in water and the solution was acidified with 2N hydrochloric acid. The precipitated N-(4-<2-(1,6-dimethyl-1,2-dihydro-2-oxoquinoline-3-carboxamido)ethyl>benzenesulfonyl)-N'-cyclohexylurea was recrystallized from nitromethane and melted at 226°–228° C.

The following compounds were obtained in an analogous manner:

N-(4-<2-(1,6-Dimethyl-1,2-dihydro-2-oxoquinoline-3-carboxamido)ethyl>benzenesulfonyl)-N'-butylurea, of melting point 194°–196° C. (from nitromethane);

N-(4-<2-(1,6-Dimethyl-1,2-dihydro-2-oxoquinoline-3-carboxamido)ethyl>benzenesulfonyl)-N'-(4-methylcyclohexyl)-urea, of melting point 203°–205° C. (from nitromethane).

EXAMPLE 7

N-(4-<2-(1-Methyl-1,2-dihydro-2-oxoquinoline-3-carboxamido)-ethyl>benzenesulfonyl)-N'-cyclohexylurea 0.8 g of N-(4-<2-(1-methyl-1,2-dihydro-2-oxoquinoline-3-carboxamido)ethyl>benzenesulfonyl)-N'-cyclohexylthiourea (melting point 208°–210° C., prepared in analogy to Example 4 using cyclohexyl mustard oil) were stirred in 100 ml of water and 100 ml of methanol with 0.32 g of yellow mercuric oxide at 60° C. for 5 hours. After filtration, the filtrate was evaporated and the residue was recrystallized from ethanol-dimethylformamide. The melting point of the N-(4-<2-(1-methyl-1,2-dihydro-2-oxoquinoline-3-carboxamido)ethyl>benzenesulfonyl)-N'-cyclohexylurea was 213°–215° C.

EXAMPLE 8

N-(4-<2-(1-Methyl-1,2-dihydro-2-oxoquinoline-3-carboxamido)-ethyl>benzenesulfonyl)-N'-cyclohexylurea 0.4 g of N-(4-<2-(1-methyl-1,2-dihydro-2-oxoquinoline-3-carboxamido)ethyl>benzenesulfonyl)-N'-cyclohexylthiourea (melting point 208°–210° C., prepared in analogy to Example 4, using cyclohexyl mustard oil) and 0.16 g of yellow mercuric oxide were stirred in 30 ml of methanol at 50°–55° C. for 5 hours. After filtration, the filtrate was evaporated and N-(4-<2-(1-methyl-1,2-dihydro-2-oxoquinoline-3-carboxamido)ethyl>benzenesulfonyl)-N'-cyclohexylisourea methyl ether was obtained as the residue.

The isourea methyl ether was heated with 5 ml of concentrated hydrochloric acid and 10 ml of dioxane on a steam bath for a few minutes. The N-(4-<2-(1-methyl-1,2-dihydro-2-oxoquinoline-3-carboxamido)ethyl>benzenesulfonyl)-N'-cyclohexylurea was precipitated by dilution with ice-water. It was recrystallized from ethanol-dimethylformamide and melted at 213°–215° C.

The 1-methyl-1,2-dihydro-2-oxo-6-chloroquinoline-3-carboxylic acid (melting point 258°–260° C.) used in Example 5 was obtained by methylation of 1,2-dihydro-2-oxo-6-chloroquinoline-3-carboxylic acid (melting point >310° C.) with dimethyl sulfate. The latter can be obtained from 5-chloro-2-nitrobenzalmalonic acid by reductive cyclization with $FeSO_4$ in ammoniacal solution.

The 1,6-dimethyl-1,2-dihydro-2-oxoquinoline-3-carboxylic acid (melting point 238°–240° C.) used in Example 6 was prepared from 1,2-dihydro-2-oxo-6-methylquinoline-3-carboxylic acid (melting point 320° C.) and dimethyl sulfate. The 1,2-dihydro-2-oxo-6-methylquinoline-3-carboxylic acid was obtained from 5-methyl-2-nitrobenzalmalonic acid (melting point 180°–182° C.) and $FeSO_4$ in ammoniacal solution.

EXAMPLE 9

N-(4-<2-(1-Methyl-1,2-dihydro-2-oxoquinoline-3-carboxamido)propyl>benzenesulfonyl)-N'-cyclohexylurea 2.0 g of 4-(2-<1-methyl-1,2-dihydro-2-oxoquinoline-3-carboxamido>propyl)benzenesulfonamide (of melting point 199°–200° C., obtained by reaction of 1-methyl-1,2-dihydro-2-oxoquinoline-3-carboxylic acid and 4-(2-aminopropyl)benzenesulfonamide in analogy to Example 1) were stirred under reflux with 1.38 g of potassium carbonate (ground) in 100 ml of butan-2-one with 0.68 g of cyclohexyl isocyanate for 4 hours. After cooling down, precipitated salts were filtered off with suction and were dissolved in 100 ml of $H_2O$, and the solution was acidified with 2N hydrochloric acid. The resulting N-(4-<2-(1-methyl-1,2-dihydro-2-oxoquinoline-3-carboxamido)propyl>-benzenesulfonyl)-N'-cyclohexylurea, which was initially somewhat oily, was recrystallized from nitromethane and twice from ethanol and melted at 183°–85° C.

The following compounds were obtained in an analogous manner:

N-(4-<2-(1-Methyl-1,2-dihydro-2-oxoquinoline-3-carboxamido)propyl>benzenesulfonyl)-N'-(4-methylcyclohexyl)-urea, of melting point 138°–140° C. (from ethanol).

N-(4-<2-(1-Methyl-1,2-dihydro-2-oxoquinoline-3-carboxamido)propyl>benzenesulfonyl)-N'-butylurea, of melting point 154°–55° C. (from nitromethane).

We claim:

1. A sulfonylurea of the formula

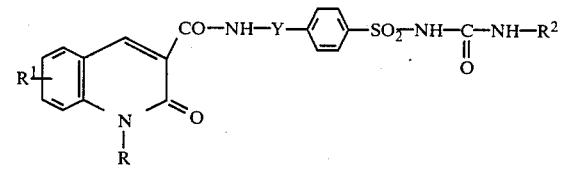

in which Y denotes alkylene having 2–3 C atoms, R denotes alkyl having 1–4 C atoms, $R^1$ denotes hydrogen, chlorine or methyl and $R^2$ denotes alkyl having 3–6 C atoms, cycloalkyl, alkylcycloalkyl, cycloalkylalkyl, cycloalkenyl, alkylcycloalkenyl or cycloalkenylalkyl, each having 5–8 C atoms, or a physiologically tolerated salt thereof.

2. A sulfonyl urea of the formula as given in claim 1 wherein R is methyl, $R^1$ is hydrogen, $R^2$ is cyclohexyl and Y is the —$CH_2$—$CH_2$-group and a physiologically tolerated salt thereof.

3. A pharmaceutical preparation for the treatment of diabetes comprising an amount of a sulfonylurea or salt thereof as in claim 1 effective to reduce blood sugar and a pharmaceutical carrier therefor.

4. A method for treating diabetes in a patient suffering therefrom which comprises orally administering to said patient a blood sugar lowering amount of a sulfonylurea or a salt thereof as in claim 1.

* * * * *